(12) United States Patent
Reichman et al.

(10) Patent No.: US 8,993,486 B2
(45) Date of Patent: Mar. 31, 2015

(54) ULTRA-HIGH THROUGHPUT SCREENING METHODS TO DETECT SYNERGISTIC DRUG INTERACTIONS

(71) Applicant: Lankenau Institute for Medical Research Chemical Genomics Center, Wynnewood, PA (US)

(72) Inventors: Melvin Reichman, West Chester, PA (US); Preston Scott Donover, Philadelphia, PA (US)

( * ) Notice: Subject to any disclaimer, the term of this patent is extended or adjusted under 35 U.S.C. 154(b) by 0 days.

(21) Appl. No.: 13/848,373

(22) Filed: Mar. 21, 2013

(65) Prior Publication Data

US 2013/0231264 A1 Sep. 5, 2013

Related U.S. Application Data

(63) Continuation of application No. PCT/US2011/052529, filed on Sep. 21, 2011.

(60) Provisional application No. 61/384,841, filed on Sep. 21, 2010.

(51) Int. Cl.
*C40B 30/00* (2006.01)
*G01N 33/50* (2006.01)
*B01J 19/00* (2006.01)
*C40B 50/08* (2006.01)

(52) U.S. Cl.
CPC ......... *G01N 33/5008* (2013.01); *B01J 19/0046* (2013.01); *C40B 50/08* (2013.01); *B01J 2219/00315* (2013.01); *B01J 2219/00592* (2013.01); *B01J 2219/00599* (2013.01); *B01J 2219/00695* (2013.01); *B01J 2219/00722* (2013.01); *B01J 2219/00725* (2013.01)
USPC .......................................................... 506/9

(58) Field of Classification Search
CPC ........................... G01N 33/50; G01N 33/5008
USPC ................................................. 506/9; 702/19
See application file for complete search history.

(56) References Cited

U.S. PATENT DOCUMENTS

| 5,865,167 A | 2/1999 | Godik |
| 2005/0161669 A1 | 7/2005 | Jovanovich et al. |
| 2008/0026400 A1 | 1/2008 | Scott |
| 2008/0311040 A1 | 12/2008 | Berry et al. |
| 2009/0233905 A1 | 9/2009 | Burke et al. |

FOREIGN PATENT DOCUMENTS

WO WO 2005051303 A2 * 6/2005

OTHER PUBLICATIONS

Kainkaryam et al., Pooling in High-Throughput Drug Screening, Curr. Opin. Discov. Devel., May 2009, 12(3), 339-350.*

* cited by examiner

*Primary Examiner* — Maria Leavitt
*Assistant Examiner* — Amy M Bunker
(74) *Attorney, Agent, or Firm* — Robert C. Netter; Kathleen D. Rigaut; Dann, Dorfman, Herrell & Skillman

(57) ABSTRACT

Synergy occurs when combined agents induce a response greater than the sum of their individual effects. The present invention provides new high throughput screening methods to detect agents acting synergistically in orthogonally pooled mixtures. Computational de-convolution of the pooled data with software reveals single-actives in the pools with twice the statistical power and with much greater efficiency than common high throughput screening approaches. Cross-correlating the orthogonal data reveals pools with activity that cannot be ascribed to any single compound. The components of such 'Orphan' activity pools are then tested individually and in all possible combination-pairs to identify and confirm synergy. The high throughput screening invention disclosed, which we name "Ultra-High Throughput Screening for Synergy (uHTSS)", is applicable for more efficiently discovering nucleic acids, proteins and small molecules that act synergistically without having to systematically test each possible pair, as is required by known screening practices.

13 Claims, 6 Drawing Sheets

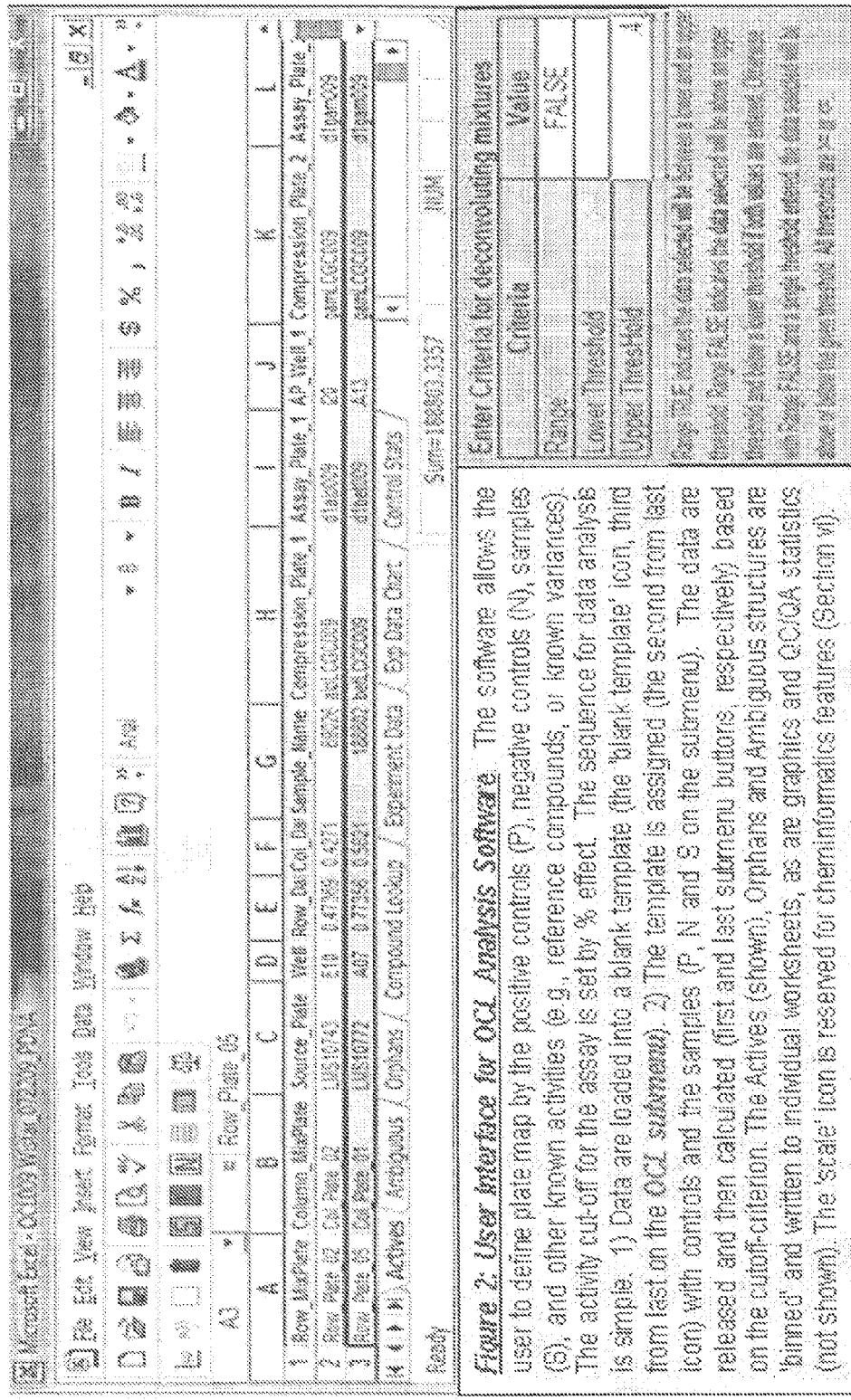

Figure 2: *User Interface for OCL Analysis Software.* The software allows the user to define plate map by the positive controls (P), negative controls (N), samples (S), and other known activities (e.g., reference compounds, or known variances). The activity cut-off for the assay is set by % effect. The sequence for data analysis is simple. 1) Data are loaded into a blank template (the 'blank template' icon, third from last on the OCL submenu). 2) The template is assigned (the second from last icon) with controls and the samples (P, N, and S on the submenu). The data are released and then calculated (first and last submenu buttons, respectively) based on the cutoff-criterion. The Actives (shown), Orphans and Ambiguous structures are 'binned' and written to individual worksheets, as are graphics and QC/QA statistics (not shown). The 'scale' icon is reserved for cheminformatics features (Section vi).

Figure 2

| Assay | Z-Score | Cutoff | Actives | Best Actives Potency | Retest Rate | Format |
|---|---|---|---|---|---|---|
| 1- E7 DNA Binding-ELISA | 0.72 | 20% | 63 | < 1 uM | 77% | ELISA |
| 2- Sugar Kinase (25-100 uM) | 0.55 | 50-70% | 48 | < 10 uM | 66% | FP |
| 3- Cathepsin C | 0.74 | 50% | 64 | 5 nM | 88% | FP |
| 4- CXCR2 | 0.72 | 50% | 7 | 5 nM | 100% | FLIPR |
| 5- USP-7 | 0.45 | 85% | 140 | 500 nM | 56% | FL |
| 6- ARE-LUC (activation)* | 0.75 | 40% | 16 | 440 nM | 96% | LUC |

Figure 4

ULTRA-HIGH THROUGHPUT SCREENING METHODS TO DETECT SYNERGISTIC DRUG INTERACTIONS

This application is a continuation of PCT/US2011/052529, filed on Sep. 21, 2011, which claims priority under 35 U.S.C. §119(e) to U.S. Provisional Patent Application No. 61/384,841, filed Sep. 21, 2010. The foregoing applications are incorporated by reference herein.

FIELD OF THE INVENTION

The present invention relates generally to high throughput screening methods.

BACKGROUND OF THE INVENTION

Several publications and patent documents are cited throughout the specification in order to describe the state of the art to which this invention pertains. Each of these citations is incorporated herein by reference as though set forth in full.

Synergy is cooperative activity between a plurality of entities to produce an effect greater than from simple additivity. Powerful combination drug therapies that have become mainstays in clinical care were all developed from previously known single therapies, many of which have dose-limiting toxicities. The rationale for combination drug therapy is that by combining medicines, a lower dose of one or both may be given to achieve the desired response with fewer side effects, or more than a single drug is required to manage the disease, irrespective of side effects. Furthermore, combination drugs acting on distinct pathways may better overcome the drug resistance that develops more readily to single agent treatments (Nature Reviews Drug Discovery 3 (2004)). Combination therapies are the backbone of clinical care for HIV, cancer and some infectious diseases (Chou, T. C. (2006) Pharmacol. Rev. 58(3):621-81; Volberding et al. (2010) The Lancet, 376:49-62). Clinicians have recognized that single-modality drugs are ineffective for treating complex disease, especially when drug resistance mechanisms come into play. Discovering innovative combination treatments earlier in the pharmaceutical R&D continuum requires a radically new drug discovery approach to high throughput screening (HTS), which currently tests only single compounds, seeking only singly-acting drugs.

Systematic discovery of multi-component therapeutics is too labor intensive for routine deployment in drug screening. As early as 1928, Loewe (Erg Physiol. (1928) 27:47-187) observed and quantified effects of combinations of compounds that were different from, and not predicted by, the activities of the constituents. The concepts of synergy, additivity, and antagonism have been explored extensively, particularly in the fields of pharmacology and toxicology (Chou, T. C. (2006) Pharmacol. Rev. 58(3):621-81). Patients with infectious diseases and those with cancer have benefited from combination chemotherapy, in many cases the standard of care (Lane, D. (2006) Nature Biotech., 24:163-164). This clinical experience—that single agents alone are insufficient to treat many diseases—has led physicians to test combinations of drugs in patients as an explicit strategy for treatment improvement. This clinical mixing has generally been conducted with agents already known to be effective in the therapeutic area of interest, or where there is a clear scientific basis for the combination.

Borisy and co-workers (Lehar et al. (2009) Discov. Med., 8:185-90) extrapolated a bench-screening method from the powerful logic of clinical combination drug testing to detect synergistic responses. Their important studies show data strongly suggesting that synergistic interactions that may be attributable to the interconnected signaling networks existing within and between cells can be detected with surprisingly high frequency, but one has to look for them. Those studies used known drugs that were laboriously paired with each other and then tested as binary pools of two drugs each. The authors developed an approach they termed combinatorial-HTS (cHTS) to prepare known drugs or other known active compounds with the aid of common automated pipettors systematically creating every possible drug pair in all possible combinations to detect all possible synergistic pairings in a library of several hundred compounds. Their cHTS approach was the basis for forming a biotechnology startup called CombinatoRx (Boston, Mass.). The approach may be useful for detecting synergistic actions in known drugs in smaller sets of pharmacologically active compounds. However, the approach cannot be used practically to detect drug synergy in the large libraries of diverse compounds typically required for HTS because the method is simply too laborious. For example, a relatively small library of 100,000 compounds results in about 5 billion unique pairs (the formula for calculating the numbers of possible pairs from a library 'n' compounds is: $(n-1)\times(n/2)$).

Conditioned screening (CS) is a recently described approach that seeks to detect new drugs that act in combination with a known drug. The CS method is the application of a screen run with and without a sensitizing amount of a known agent in order to identify new drugs that enhance the effect of the known agent (i.e. drug). This offers a powerful approach to identify new agents that are effective only in the presence of the known drug. When used to discover agents which kill under the sensitizing condition, this approach is termed a screen for a 'synthetic lethal' (Iglehart et al., (2009) N. Engl. J. Med., 361:189-191). Conditioned screening has been described as HTS for Synergy (HTSS) when used to discover agents that are synergistic to the actions of a drug to which resistance has developed. In the example described in published work (Zhang et al. (2007) Proc. Natl. Acad. Sci., 104:4606-11), a microbial natural product library of 20,000 extracts was screened for hits that synergize the effect of a low dosage of ketoconazole (KTC) that alone shows little detectable fungicidal activity. A known drug, beauvericin, dramatically synergized KTC activity against diverse fungal pathogens as determined in a checkerboard assay.

Like cHTS described above, HTSS has been shown useful in standard bioassays to experimentally detect combination drugs that may have desirable synergistic actions. However, this approach also suffers from the limitation that only a single known drug is tested for synergy against a library of random compounds. It would be extremely useful to develop a method that could detect drug synergy in any bioassay, with any large chemical library—no matter how large—with far greater efficiency than methods hitherto described.

SUMMARY OF THE INVENTION

In accordance with one aspect of the instant invention, methods of identifying agents that exhibit synergy are provided. In a particular embodiment, the method comprises a) performing orthogonally pooled screening on pooled mixtures of agents using an assay to measure the activity of the pooled mixtures; b) isolating active pooled mixtures detected in step a) that exhibit no singly active agent; c) verifying that no summation of uncombined agent activities, from any subset of agents therein, achieves the level of activity of the isolated active pooled mixture (e.g., by individually testing each agent from the isolated active pooled mixture detected in step b); and d) testing binary mixtures comprising every possible pair of agents from all agents within a verified isolated active pooled mixture identified in step c); wherein the agents of a binary mixture exhibit synergy when the binary mixture exhibits greater activity than the sum of the individual activities. In a particular embodiment, the orthogonally pooled screening comprises generating self-deconvoluting plates. In a particular embodiment, the pooled mixtures further comprise an additional agent, particularly an inactive agent. The assays of the instant methods may be any assay to detect a property of interest (e.g., binding of a compound of interest, effect on enzymatic activity, etc.).

BRIEF DESCRIPTIONS OF THE DRAWING

FIG. 1 is a schematic depicting a 10×10 matrix of 96-well plates orthogonally cross-pooled to yield 20 orthogonal pooled screening (OPS) plates.

FIG. 2 provides an image of a user interface for analysis software to identify single Active agents versus Orphan pools, the latter being those that display high activity but do not appear to contain any single-active agent.

FIG. 3 provides a frequency plot for the three categories of actives representing averaged response from several assays.

FIG. 4 provides a table of assay results which demonstrate a high retest confirmation rate for the assignment of the single Actives, thus validating that the software can discriminate single-Actives in pools.

DETAILED DESCRIPTION OF THE INVENTION

Figure 1:
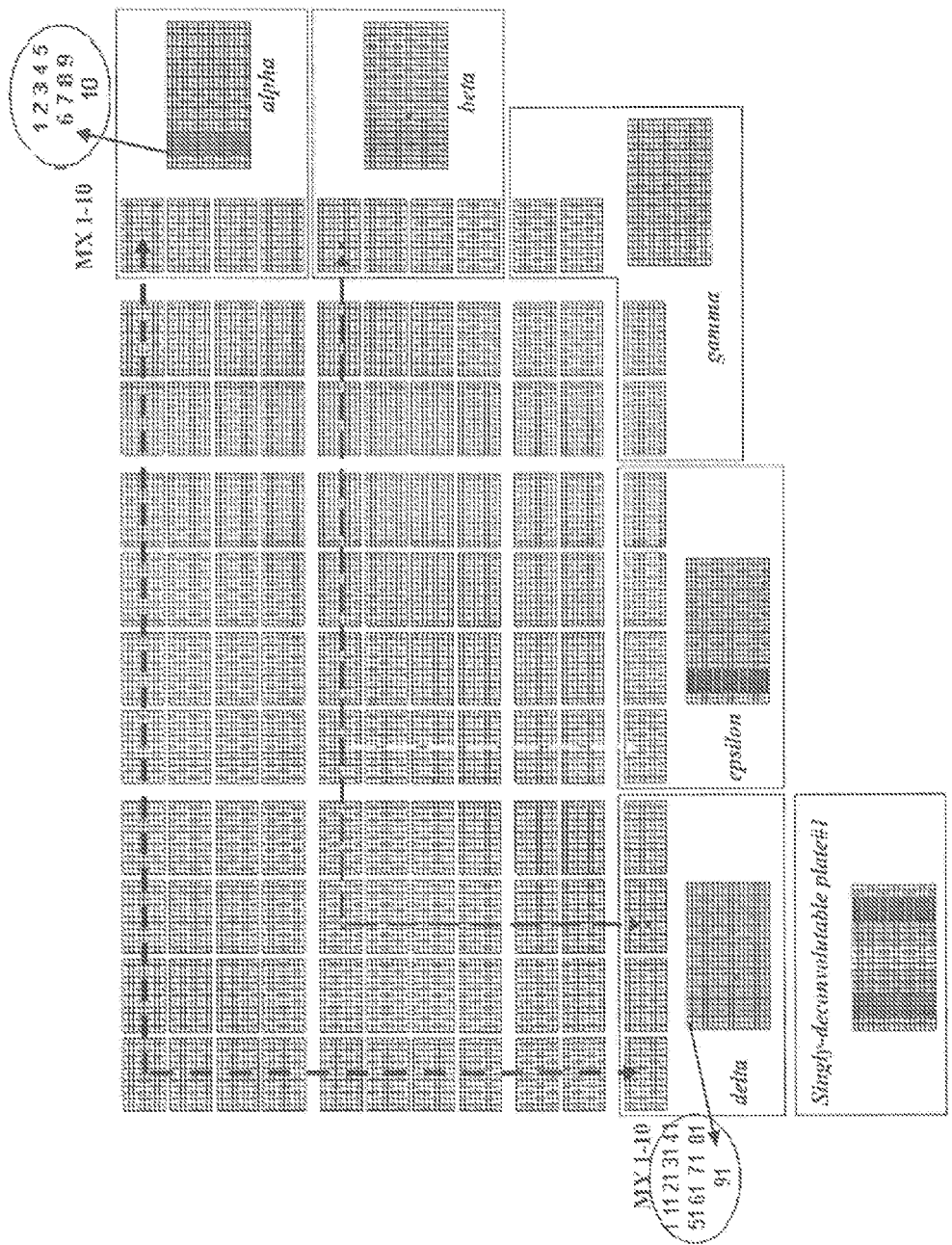

The instant invention describes a new method that enables drug discovery research scientists to detect drugs that work synergistically in combination to elicit desired pharmacological responses. The method describes the use of a highly efficient drug screening protocol relying on compound pooling and a new way to analyze the drug screening data to discover combination drug treatments acting via interacting cell-signaling pathways. The agents to be screened by the methods of the instant invention can be any compounds (e.g., isolated compounds), particularly any natural or synthetic chemical compounds (such as small molecule compounds (including combinatorial chemistry libraries of such compounds), extracts (such as plant-, fungal-, prokaryotic- or animal-based extracts), organic compounds and molecules, inorganic compounds and molecules (e.g., heavy metals, mercury, mercury containing compounds), biological macromolecules (such as saccharides, lipids, peptides, proteins, polypeptides and nucleic acid molecules (e.g., those encoding a protein of interest), inhibitory nucleic acid molecule (e.g., antisense or siRNA), and drugs (e.g., an FDA approved drug). In particular embodiments, the method of the instant invention (called ultra-high throughput screening for synergy (uHTSS)) is characterized by at least one of:

1. Acquiring bioassay data far more (e.g., 500% more) efficiently than by prevailing HTS practice using OPS as described herein that distinguishes the activities of all singly-acting compounds from those in Orphan pools, namely those pools displaying activity that cannot be resolved to activities of single compounds. OPS employs efficient testing of pooled entities thereby affording the opportunity for detecting serendipitous synergistic interactions by looking for them in a new way described herein.

2. Ranking 'Orphan' pools most likely to contain active pairings based on their estimated pool scores calculated from screening orthogonally pooled compound arrays.

3. Cherry-picking individual compounds from nominated Orphan pools, recapitulating the 10-pools and retesting serial dilutions of those pools as well as the individual compounds.

4. Determining pairs of compounds with synergistic activity by testing all possible paired combinations from those Orphan pools that confirm only when all the individual compound components are recapitulated again as a pool and not when tested individually.

5. Characterizing the paired-hits detected by the disclosed method by retesting the compounds serially diluted individually and together at constant ratio dilutions.

6. Searching online databases for similarity of pair-members to known drugs to infer mechanism;

7. Validating putative biological mechanism by recapitulating activity with reference surrogates or antagonists;

8. Performing cross dilution combination experiments to assign pharmacological mechanism (additive synergy or potentiation) as well others described in scientific publications (Chou, T. C. (2006) Pharmacol. Rev. 58(3):621-81; Zhang et al. (2007) Proc. Natl. Acad. Sci., 104:4606-11); and/or 9. Ultimately, testing agent pairs in relevant disease models to discover and validate pairings that act synergistically to quench diseases that resist single agent treatment.

The disclosed uHTSS method described, that relies on orthogonal pooled screening (OPS), is an elegant and powerful screening strategy whereby single-actives are reliably detected in 10-pools, without the need to 'explode' pooled wells into their individual compounds for separate testing in order to determine the active compound (Motlekar et al. (2008) Assay. Drug Dev. Technol. 6:395-405). In the embodiment described and depicted in FIG. 1, using 100 source plates in all, the compounds contained on ten microtiter source plates are combined into a single target plate, the operation carried out twice for each source plate, and therefore each source plate appearing in two separately prepared target plates, orthogonal to one another, i.e. sharing no other common plate between them. FIG. 1 depicts a 10×10 matrix of 96-well plates orthogonally cross-pooled to yield 20 OPS plates (e.g., black arrows, showing pooling across 10-rows in the 100-plate matrix to yield MX1-10; and then pooling the same matrix vertically to yield MY1-10). Since 384-well microplates are the most common HTS format, the twenty 96-well plates may be condensed into five 384-well plates labeled alpha-epsilon in FIG. 1.

In essence, the entire library is pooled twice in orthogonal directions. Each compound is presented twice, in different wells, mixed each time with nine other compounds, as shown by the wells marked with balloons containing ten numbers, representing ten compounds in a pool. The first well of the 384-well compression-plate alpha contains compounds 1, 2, 3 . . . 10, stemming from the first well of plates 1-10 (ten ROW-1 plates as shown by the black horizontal dashed-arrow) in the matrix. The first well of the 384-well compression-plate delta again contains compound-1 with nine other compounds, stemming from plates 11, 21, 31 . . . 91 (10× COLUMN-1 plates as shown by the black vertical dashed-arrows) in the matrix. Only compound-1 is common between the two wells. FIG. 1 depicts how deconvolution works for single active compounds.

There are three categories of activities that typically result from OPS data at a given activity-cutoff, which special software to de-convolute the pooled data may identify (see FIG. 2). First, unambiguously correlated 'Actives' are those hits (i.e., active compounds) that unambiguously deconvolute to a single compound, as represented by the grey arrows in FIG. 1. Second, 'Ambiguous' correlation of actives are instances where, in addition to the two actives at the grey arrows, an additional apparent active in one of the arrays appears in the same row (or column), as shown by the white arrow. Here, three active wells in the two orthogonal arrays can be traced back to two compounds. Such 2:1 deconvolutions result in two 'Ambiguous' actives. In assays with low hit rates it is unlikely that two active compounds appear in any one well; rather, it is much more likely that the activity detected in a co-axial well results from the chance coincidence of a pool of minor activities that happen to fall coaxial with a correlated active-but-only retesting both compounds will reveal the true active. Third, 'Orphan actives' are activity instances occurring in one orthogonal array only. Orphans can result from: a) spurious noise, b) from true activity which achieves the cutoff in one array, but not in the other, or c) additive or synergistic effects from two or more compounds uniquely paired in that single well. Detecting the latter is the basis of the present invention, as described herein below.

A limitation with the pooling approach described in the literature is that the OPS plates must be screened together as a correlated set, since no single plate contains both orthogonal instances of any compound. For example, if the five plates (alpha-epsilon as in FIG. 1) are screened, but one or more plates fail, then the OPS data analysis (described below) is compromised. The failed plate must be re-screened. However, if its basal activity (i.e., 'solvent control' readout) changes due to intrinsic variability or for other reasons, the results from the re-screened plate can be skewed relative to the other four plates, and thereby skew the validity of the data from the entire set.

The method of compressing 100:20:5 orthogonal-pooled plates depicted by FIG. 1 is described (Motlekar et al. (2008) Assay. Drug Dev. Technol. 6:395-405). A new self-deconvolution arrangement, which is not obvious from previously described art, is represented (FIG. 1, bottom box) by the multi-shaded plate sourced from the original five condensed plates. This rearrangement yields five 384-well plates (only one is shown), each of which contains both instances of every compound contained thereon, and thereby making each such plate an independently assayable and self-deconvoluting mini-library. This self-deconvolution arrangement, which has not been described in the published literature, has the advantage of allowing a single 384-well plate containing up to 1920 compounds in duplicate to be screened and deconvoluted alone, without any interdependency on other plates, so that if an error occurs on one plate, it affects only that single plate, but does not affect the entire set of plates. In the methods described in the literature, the interdependency between plates is an added source of error—especially if operator errors occur. Sometimes, such operator errors are unknown. By eliminating errors in OPS stemming from plate interdependencies, the instant invention improves the precision of the approach and the validity of the data, which increases the precision of the data, this is important for the success of the new invention, which uses OPS to detect combination pairs of agents that may act synergistically, as described further below.

Common analysis software methods for mining HTS data operate on a single dimension of activity, i.e., individual compounds are assigned a binary activity; namely, as potentially active or not based on the observed activity relative to the mean and standard deviation (SD) of activities observed for the entire population of compounds tested. For example, an activity cutoff of greater than 3SD from the mean is commonly used for assigning compounds as apparent actives. Alternatively, a simple activity cutoff is defined. For example, all compounds whose activities are greater than 50% inhibition (or 2-fold stimulation, etc.) are assigned as active. The compounds selected as potentially active are then 'cherry-picked' from the library for confirmation retesting, determination of potency, selectivity, toxicity, etc. As described above, there are three categories of activities, rather than a single category, that can result from OPS data. A data visualization method helps to ascertain the relationships between the three inter-related activity categories.

Figure 3:
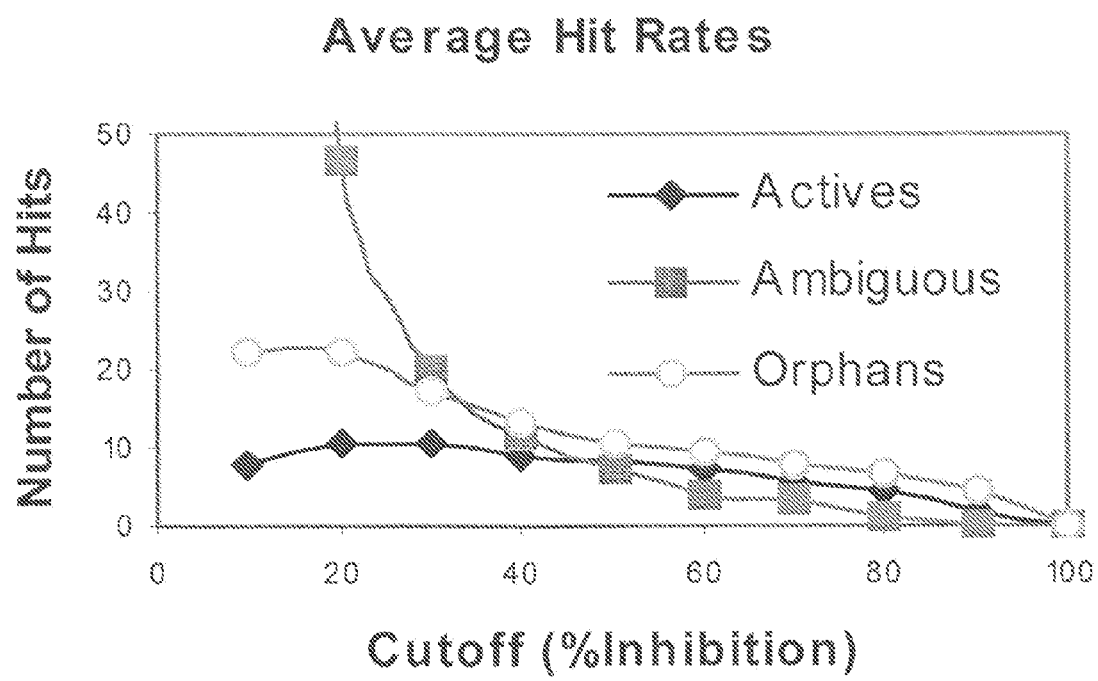

A software is provided herein with a graphical user interface (FIG. 2, above) comprising a new data mining method of the instant invention called 3-dimensional data triaging (3DDT) that allows simultaneous visualization of three activity classes at graded cutoff levels in order to assign an appropriate activity cutoff for OPS data. Frequency plots for the three categories of actives are shown illustrated by FIG. 3, representing averaged response from several assays. As the activity cutoff increases (from 0%-100% inhibition of the response), the Ambiguous actives count falls exponentially while the Actives category remains relatively constant. Excellent retest confirmation rates for Actives have been found (see FIG. 4) at an activity cutoff determined at the intersection of the Ambiguous curve and the Active curve. At this nexus, it has been found that confirmation rates for Actives (FIG. 4) are on average around 80% and almost 50% for Ambiguous, which is close to the maximum value expected, since one-half the Ambiguous hits are expected to represent a 'true' single-Active by chance located coaxial to an Orphan (as discussed above for FIG. 1). The Actives signal remains stable over a wide range of cutoffs, suggesting this category clearly represents pharmacological activity, an interpretation supported by the good retest outcomes in FIG. 4. As the cutoff is made more stringent, there is dynamic equilibrium between scored hits transiting from Ambiguous to Active, presumably discarding coincident minor activities in the other dimension; simultaneously, Actives falling below the cutoff in one orthogonal dimension become orphaned.

The triaged categories in the instant OPS protocol data behave with reproducible patterns in both biochemical and cellular drug screening assays. The behavior of the Ambiguous curve follows exponential decay, suggesting that at the lower cutoff values (i.e., low stringency), the activity is due to 'noise', which dissipates as cutoff stringency increases (see FIG. 3). The average of the Actives retest rates is 80% (FIG. 4), which is quite good by HTS typical standards, supporting that orthogonal-correlated activities detected by the software at appropriate cutoffs are not spurious noise.

The software described herein allows tabulating and visualizing all three expected activity categories in data arising from bioassays using OPS. At thresholds where the 'Ambiguous' activity approaches zero, suggesting that 'noise' in the assay is extinguishing, the number of Orphaned (i.e., non-correlated) pools is greater than any other category (FIG. 3). The activity observed from 'Orphaned' pools, after assay noise has been minimized, must be due to the combined actions of more than one compound, or masking of a singly active compound's contribution in the other array. It is critical, therefore, to eliminate all singly-acting compounds in order to correctly determine Orphan compound pools.

To ensure the most efficient extraction of all actives, another novel approach was applied called promiscuously descending activity cutoffs (PDAC). The activity cutoff is assigned and set around the point where the Ambiguous curve crosses the Actives curve (a point where the probability of correlated activity is greater than uncorrelated assay noise). All 2-D correlated activities observed at this cutoff; i.e., the Actives and the Ambiguous, are selected for retesting. The stringency of the activity cutoff is the lowered by 5% or lower increments to as low a cutoff as 20% (the lowest percentage inhibition activity cutoff described in the literature (Motlekar et al. (2008) Assay. Drug Dev. Technol. 6:395-405), or even as low as 2SD from the mean, and all the new Actives (and only the actives) that appear at each new cutoff are recorded. The purpose of doing so is to help ensure that—insofar as it is possible by HTS—the structures of any and all Actives are identified, even weaker actives that are typically ignored in typical HTS because their activity is below the assigned activity cutoff for the screen, which on average is usually 50% of the maximal obtainable response or 3SD from the average response. The reason this is important for the method of the invention is to isolate those 'Orphan' pools whose observed activity cannot be ascribed to additive action of weak actives. The software-enabled method disclosed accomplishes this objective, as described below.

The Orphan category (an active pool whose activity cannot be ascribed to a single orthogonally-correlated Active) dominates at greater stringency activity cutoffs where the retest rate for the orthogonally-correlated Actives approaches 100% and, importantly, the count of Ambiguous-actives approaches zero (see FIG. 3). There are three possibilities that may underlie Orphan pool activities observed at or close to the maximum obtainable response for the assay: a) an efficacious 'true' Active was detected in one orthogonal pool but not the other, hence rendering the former an apparent (false) orphan pool; b) several weak single actives (weak-Actives) display additivity in the apparent bioassay response; and c) a combination pair acts synergistically together, but neither is active singly. If cases a) and b) are eliminated from consideration, the activity in the remaining Orphan pools must be due to combination-pair synergy, which the novel method described herein will detect.

Figure 5:
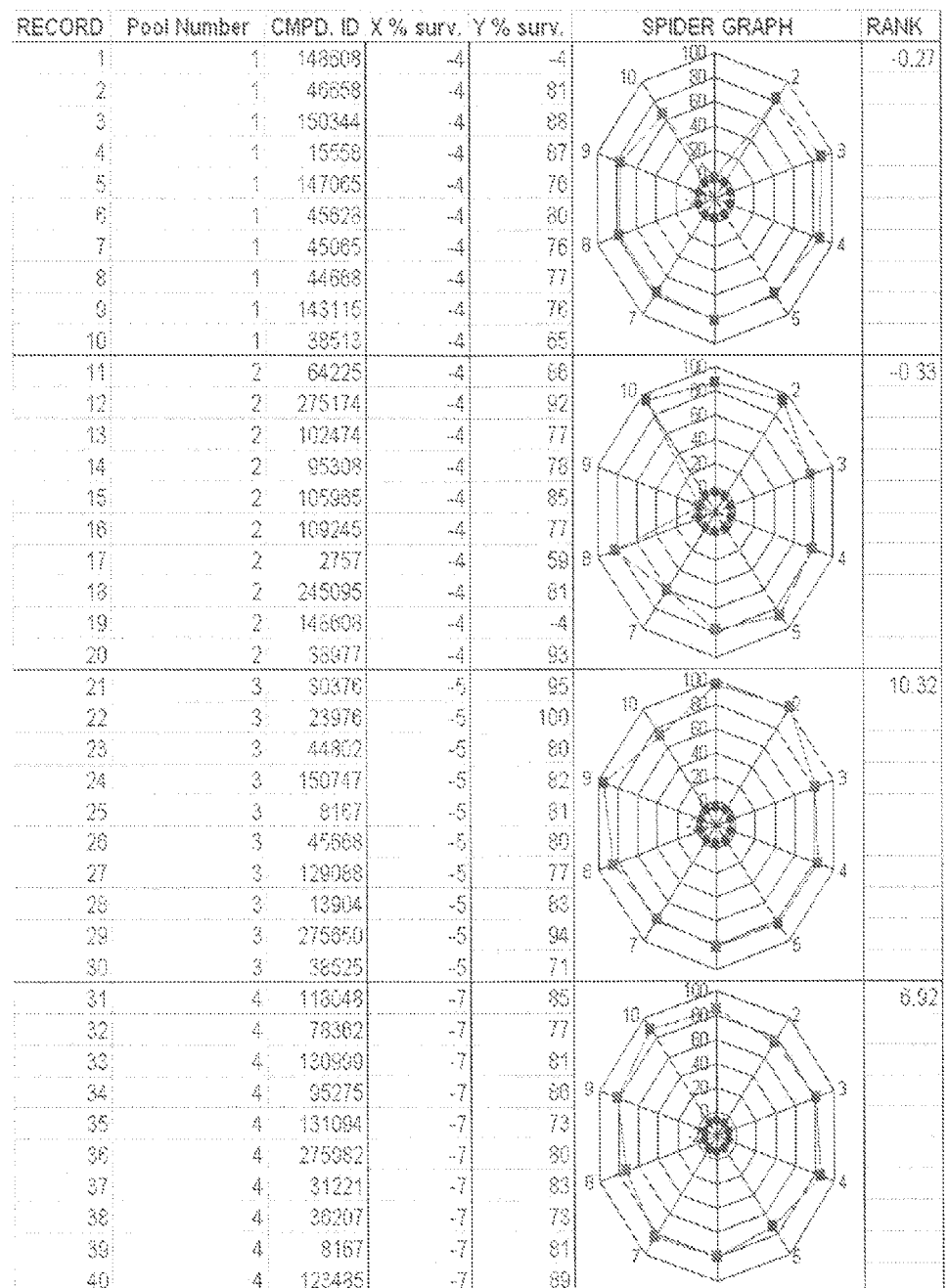
FIG. 5 depicts a method for confirming that single actives do not account for the activity in the Orphan pool.

The possibility (a) that a true active may be missed in OPS due to its failure to manifest orthogonally-correlated activity may be referred to as a false Orphan positive. It may be that there is some masking (blocking) activity in one pool containing the active and not the other pool. Therefore, the orthogonal activities of all ten members of all Orphan pools that show activity attaining the assigned cutoff may be interrogated as depicted by FIG. 5, which shows four representative orphan pools, each containing ten compounds, with the apparent activities of all the pools in the 'X' orthogonal dimension observed to be extremely active at –4% survival (Pool 1), –4% (Pool 2), –5% (Pool 3), and –7% (Pool 4) survival, respectively. In essence, all four pools yielded total inhibition.

Assuming that the activity cutoff is assigned as <20% survival, relative to the solvent control, the data analysis method reports the orthogonal activity in both ('X' and 'Y') pools for every Orphan well assigned as Active (i.e., <20% survival). The algorithm compares the activity of the individual compounds comprising the 'X' active-Orphan pool (wherein all the compounds are assigned the activity of the 'X' pool) with the activities of these individual compounds observed in their other ten ('Y') pools. It may be seen from the example in FIG. 5 that the first two pools contain compounds whose activity in the 'Y' pools are –4% and 65% survival, respectively (compounds 148608 and 38513), each insufficient to achieve the activity-cutoff of 20% or less survival, but their combined effect is too great to simply be ignored. It may be that experimental error or a blocking activity of another compound in the 'Y' pool caused the orthogonal cutoff of 20% survival to be missed. The 'bulls-eye' radial graphs are a convenient way to depict that the apparent Orphan-active pool may be due to additive activities not coincident in the orthogonal pools. Compounds whose scores lie at the outermost perimeter of the radial plots present activities not significantly different from the solvent control at 100% survival (0% inhibition). Compounds yielding 0% survival (100% inhibition) have scores at the center of the plot. The plots for the first two pools show that each contains an active compound in the 'Y' pool, exhibiting a significant deflection towards the center of the plot. Multiplying the % Solvent Control 'Y' pool values for the ten compounds (×100) yields an estimate of the activity of their combination in the 'X' pool, their values are –0.27 and –0.33 in pools 1 and 2. In contrast, the estimated activities of Orphan-active 'X' pools 3 and 4 yielded 10.32 and 6.92. The higher these values are (which are the product of all the % survival values×100), the less likely it is that the potent inhibition observed for the 'X-pool' is due to simple additivity of effects. All the compounds in the bottom two pools of FIG. 5 appear 'clean' (inactive), with no single compound eliciting less than 70% survival in the 'Y' pools. All activities in pools 3 and 4 are close to the outer circumference of the radial plot that represents the activity of the individual compounds in the 'Y' pool. These estimates form the basis for rank ordering pools as it is expected that lower percentages likely indicate pools containing compounds with additive activities and higher percentages derive from pools harboring another activity, possibly a synergistic pair of compounds.

Orthogonal pools where complete activity is observed in one dimension ('X') but for which no individual appears to account for the activity—by virtue that they are all relatively inactive when appearing in their other pool—likely derive their activity from either: 1) additivity of masked, weakly-acting compounds, or 2) a 'synergistically' active combination pair. The disclose uHTSS method can be used to isolate Orphan pools whose profound activity is likely from an active-pair of compounds working efficaciously in concert, rather than any single active, or the summation of a number of weak actives. With such Orphan pools isolated to a relatively small number of instances (e.g. two pools for every 8,000 compounds, or 1600 pools, or around 1/1000), their individual compounds can be 'exploded' (separated) and tested individually in three distinct experimental settings: A: recapitulating the activity of active orphan pool (i.e., confirmation retesting); B: testing each compound singly to verify that the pooled activity can be assigned to no single compound nor sum of weak activities in the pool; and C: pairing each compound with each other to discover an active-pair combination; for every pool of ten compounds, there are 45 combination pairs. The methods for these tests are described below.

Recapitulating the activity of active orphan pool (i.e., confirmatory retesting) may be accomplished by 'cherry-picking' the ten individual compounds that comprise the active pool and testing them individually and in combination as in the original 10-pools. The individual compounds and the 10-pool are both serially diluted to determine: a) whether the originally-detected Orphan activity confirms on retest, and if so, its potency and; b) whether a single compound alone can account for the activity observed in the 10-pool in the primary OPS assay; and c) whether there are several compounds that are weakly active and whose activities directly add up to the activity of the original pool. Serially diluting (typically in ½ log steps) the compounds in the bioassay—starting with the stock concentration at 10-fold above the original concentration in the primary OPS assay—allows determination of the potency of the individual compounds, if active. Likewise, assaying serial dilutions of the pool provides a direct comparison. It may be that several of the individual compounds in the 10-pool are weakly active and the activity of the Orphan 10-pool is due to pharmacological additivity, rather than synergy. Otherwise, the activity of the 10-pool is due to a combination-pair acting synergistically (e.g., neither compound is significantly active alone, but together are active in combination).

It is desirable to eliminate from consideration pools containing two or more compounds that are weakly active and whose additivity accounts for the activity in the Orphan 10-pools. The Orphan pool retesting method calls for retesting at the original concentration and also testing the individual members at, for example, a starting concentration 10-fold higher than that attained in their component 10-pools; and also retesting the recapitulated pool at 3-fold higher and 3-fold lower concentration than originally tested. Those pools whose activity can be clearly accounted for by additive effects from individual components are eliminated from further consideration. An example would be if the activity cutoff for the assay is assigned at 50%, and three compounds from a single active Orphan pool are detected as weakly active, each with activity of 33% of the maximal response, together yielding an apparent maximal response additively when combined in a 10-pool. On the other hand, it may be possible that a single active compound that was missed in the primary OPS assay accounts for the activity in the 10-pool. For example, the activity of a true active compound could be masked in one orthogonal array by a masking compound contained in that 10-pool but not in the other, hence making a true single active compound appear as an Orphan pool. The retest dilution scheme described above is designed to eliminate Orphan pools whose activities can be ascribed to an individual compound or simply additive compound activities.

If any active 10-pools cannot be resolved to a single compound, and also cannot be accounted for by pharmacological additivity from weakly-active individuals, then each possible combination of the individual compounds is tested. Others have described in detail how to systematically mix and dilute compounds to detect combination-pair activity wherein every member of a population of compounds (i.e., the components of every 10-pool imputed as potentially arising from synergy) is systematically combined with one another; there is no new art in this step, nor subsequent steps that enable resolving the mechanism of action for the synergy (Chou, T. C. (2006) Pharmacol. Rev. 58(3):621-81; Lehar et al. (2009) Discov Med., 8:185-90). The instant invention describes herein how to isolate those pools (Orphans) that are most likely to contain synergistic-pairs.

In a particular embodiment, the instant invention of uHTSS provides a high throughput screening (HTS) method to detect active-pair combination agents that act synergistically in pooled compound library mixtures. In a particular embodiment, the uHTSS method comprises the following steps:

I. A matrix (e.g., 10×10=100 plates) of microplates (e.g., 96-well microplates comprising 12 columns by 8 rows) is orthogonally cross-pooled to yield orthogonal pooled screening (OPS) plates (e.g., 20) by the following (sub)steps:
  i. Successively combining (e.g., with the aid of an automated pipetting device) an equal aliquot (e.g., 10 microliters) from each of the 10 plates in the first row of the matrix (10×10) in turn into a single pooled-destination plate so that each well of the 96-well pooled plate contains 100 microliters of the combination of the ten×10 microliters of individual compounds from each corresponding well of the ten 96-well source plates from the first row of the source-plate matrix, and successively repeating the 10-into-1 plate pooling by rows for all 10-rows in turn that comprise the 100-plate source matrix, so that a representative aliquot from each plate of the original 100-plate matrix is contained in 10-pooled plates, with each pooled row plate representing an entire row of 10 individual source plates.
  ii. Successively combining (e.g., with the aid of a pipetting device) an equal aliquot (e.g., 10 microliters) from each of the ten (10) plates in the first column of the (10×10) matrix in turn into a single pooled-destination plate so that each well of the 96-well pooled plate contains the combination of the ten individual compounds from each well of the ten 96-well source plates from the first column of the source-plate matrix, and successively repeating the 10-into-1 plate pooling by columns for all 10-columns in turn that comprise the 100-plate source matrix, so that the original 100-plate matrix is represented in the 10-pooled plates, with each pooled column plate representing an entire column of 10 individual source plates.
  iii. The wells of the OPS plates (e.g., 20×96-wells) are transferred to new plates (e.g., five 384-well plates) for higher density screening formats.
  iv. The wells transferred in iii are rearranged into a final configuration wherein the pools on each separate plate always contain both representations of each compound on that plate. That is to say, the pools are transferred such that every compound on each plate is represented twice on that plate. This renders each plate a 'self-deconvoluting' OPS plate, and hence any failed plate does not taint the others and no plate depends on another for deconvolution.

II. The self-deconvoluting OPS plates are tested in HTS bioassays as per the typical protocols in the field of drug screening bioassays.

III. The screening data from the bioassays on the self-deconvoluting OPS plates are then analyzed (particularly by a computer program) to detect four categories of active wells based on the desired activity cutoff value, as enumerated by i-iv below.
  i. Unambiguous orthogonally-correlated active compounds ("ACTIVE"), are those instances such that only a single compound shared by only two orthogonally active 10-pools could account for the activity observed in those 10-pools.
  ii. "AMBIGUOUS" correlation of actives are instances where, in addition to the two active pools achieving the activity criterion value pointing to one active compound, an additional apparent active in one of the orthogonal arrays appears in a pool coaxial with an otherwise ACTIVE compound, making three active wells in the two orthogonal arrays traceable back to more than a single compound.
  iii. "ORPHAN" actives are activity instances occurring in one orthogonal array only, which can result from: a) spurious noise; b) from the activity in one array achieving the cutoff but not in the other; c) additive or synergistic effects from two or more compounds; detecting the latter is the intent of the Method of this invention.
  iv. Weakly ACTIVE compounds are orthogonal-correlated activity instances just as in the 'ACTIVE' category, except their activity falls below the assigned cutoff.

IV. The bioassay data for the three categories of activities i-iii described above by Step III are plotted automatically or manually with 'Activity' (i.e., % response; on the X-axis) versus (number of) Instances for each active category (e.g., on the Y-axis), as depicted in FIG. 3.

V. The activity cutoff for the assay is then assigned so that the vast majority (=>99%) of the compounds score as inactive.

VI. All orthogonally-correlated Actives (Active, Ambiguous, and Weakly-Active) are then 'cherry-picked' as individual compounds, and then retested in the bioassay to confirm their activities.

VII. The activity in Orphan pools that cannot be accounted for by structure-activity relationships learned from the confirmed single compounds are then isolated and their individual compound components are retested, along with the recapitulated pools, to isolate and confirm those orphan pools whose activity cannot be accounted for by any individuals acting alone or summating additively, thus indicating a synergistic interaction in those pools.

VIII. The individual compounds in the confirmed Orphan 10-pool are then tested in all 45 possible combinations to isolate the synergistically acting compounds.

In a particular embodiment, the chemical library is screened twice, by standard 'n=1' HTS and by OPS. Results from these 'stacked' HTS studies support that OPS appears to detect all the single actives in the library, even when using an activity cutoff as low as 20% of the maximal response (Motlekar et al. (2008) Assay. Drug Dev. Technol. 6:395-405). By running OPS together with standard HTS, every compound garners three data points (two from OPS and one from HTS), which is the 'gold standard' for bioassay data. Once all the actives are assigned, it can be determined whether the activity in Orphaned pools is due to a single active that was missed in the orthogonal array, or whether two or more the structures in the pools with weak activities added together. For those pools where activity cannot be ascribed to additive effects, the individual compounds in the pool may be tested by the method depicted in FIG. 5 to confirm that single actives do not account for the activity in the Orphan pool. The basis of the activity can then be investigated by systematically combining all component compounds with one another to determine the synergistic combination pair that elicits the observed activity. Noteworthy is that the stacked HTS+OPS yields three data points for every compound. Moreover, the 'overhead' for acquiring stacked n=3 data as described is only 20% greater than running standard HTS, by virtue that OPS is 5-fold more efficient than standard HTS. If the objective for a stacked screen is to detect synergistic drug interactions in pooled libraries and acquiring n=3 data as described immediately above is not as important, or resources cannot accommodate the added 20% in overhead required for stacking OPS with standard HTS, then running simple 10-pool screening (only one dimension from the OPS arrays) together with standard n=1 HTS will allow extraction of the active compounds from all active pools, leaving behind only those pools whose activity may be accounted for by synergistic drug interactions. This paradigm requires only 10% additional overhead over a standard screen.

In a particular embodiment, conditional screening to discover new anti-infectives, for example, may be accomplished by adding to the growth medium of the microbe under investigation a drug to which the pathogen (e.g., virus, bacteria, etc.) has developed resistance. The HTS compound library is added at an appropriate single concentration and growth is initiated. All actives are retested in the presence and absence of the conditioning agent. All compounds that inhibit in both conditioned and neat settings may represent new anti-infectives with efficacy in drug-resistant strains. However, compounds that are active only in the presence of the conditioning drug represent a synergistic drug interaction, defined here as combinations where neither agent works alone, but only in combination. Discovering such agents can be very effective tools to probe the basis of drug resistance. For example, if the mechanism by which the conditional new drug reverses resistance to the classic drug can be resolved, then new generations of anti-infective drugs less prone to resistance, or even agents that can reverse resistance to otherwise effective drugs, could be developed earlier in the R&D continuum. Running such a conditioned screen in the OPS format has never been described. The method described herein affords 500% greater efficiency than prevailing practices disclosed in the field, allowing for multiple test conditions on the same library, or increasing the library size by five-fold, requiring the same effort as a library ⅕th the size screened with one test compound in each well, rather than 10-pools.

Unexpected synergistic interactions of diverse compounds with cellular signaling activities may be attributable to the interconnected signaling networks existing within cells. However, in the conditional screening just described, only a single agent is added to every assay well in OPS formatted bioassays in order to detect new compounds synergistic to the added agent. Such limited combinations as formed when using a conditioning agent explores only the 'tip of the iceberg' of combination space. Increasing the diversity and quantity of chemical scaffolds used as conditioning agents—by including approved drugs, drugs showing clinical activity but that were not approved, reference pharmacological agents (i.e., chemical probes of certain pathways, but that never were developed for the clinic) and others and testing in diverse biological systems—increases the chances of finding new leads that synergistically enhance the activity of known therapeutic agents.

Library-focused HTSS is the orthogonal pooling and testing of libraries of compounds highly enriched with many core scaffolds designed to actively modulate specific signal transduction mechanisms in bioassays seeking interacting pathways that modulate cell responses synergistically. For example, libraries that were designed to modulate kinases, GPCRs, ion channels, etc., can be combined together by orthogonal pooling and tested. The likelihood that modulators of specific signaling transduction pathways will interact together on more than one cell signaling pathway is higher than that in OPS with 'random' chemical libraries that are not so enriched with pharmacologically active compounds.

Pharmacologically active compounds may be pooled together to greatly increase the frequency of synergistic drug interactions in OPS. However, doing so may lead to too many hits from additive actions of similar compounds in the pooled wells, causing an inordinately high level of general assay 'noise', which may compromise the efficient extraction of orthogonal-correlated actives, and subsequent isolation of Orphan pools. In fact, one of the elements for success of OPS is to avoid pooling molecules with similar structures, which would cause 'collisions' between like analogs, leading to summation of activities and false positives, rather than detection of true synergistic effects (Katja et al. (2006) Technometrics 48:133-143). There are two solutions for this. First, structurally focused libraries containing analogs of compounds that modulate known signal transduction pathways can be pooled, but screened at a lower concentration than diverse (non-focused) libraries, so that the 'noise' of additive activities becomes reduced. Alternatively, the focused libraries containing similar structural themes (i.e., scaffolds) could be arrayed on separate plates, which are then aligned along the 'diagonals' of the source matrix (i.e., a 10×10 array=100 plates). Each diagonal line (see FIG. 6) may contain congeneric plates of 'structure-focused' compounds, on which each plate would be combined with nine plates of dissimilar compounds coaxially across rows and columns, respectively. By this method of 'seeding' diverse orthogonal-pooled molecules with class-focused molecules together, the likelihood of detecting synergistic actions is greatly increased, while avoiding excessive noise due to coincident pooling of like structures.

In a particular embodiment, uHTSS is used to screen siRNA. Small interfering ribonucleic acid (siRNA) screening studies have become a standard experimental approach for target identification and target validation in drug discovery, and siRNAs and microRNAs (miRNAs) are even being developed as potential therapeutic agents. The RNA interference pathway is often exploited in experimental biology to study the function of genes in cell culture and in vivo in model organisms. Double-stranded RNA is synthesized with a sequence complementary to a gene of interest and introduced into a cell or organism, where it is recognized as exogenous genetic material and activates the RNAi pathway. Using this mechanism, researchers can cause a drastic decrease in the expression of a targeted gene. Studying the effects of this decrease can show the physiological role of the gene product. Since RNAi may not totally abolish expression of the gene, this technique is sometimes referred as a "knockdown", to distinguish it from "knockout" procedures in which expression of a gene is entirely eliminated (Azorsa et al. (2010) BMC Genomics 11:25). Despite the proliferation of promising cell culture studies for RNAi-based drugs, some concern has been raised regarding the safety of RNA interference, especially the potential for "off-target" effects in which a gene with a coincidentally similar sequence to the targeted gene is also repressed. A computational genomics study estimated that the rate of off-target interactions is about 10%. One major study of liver disease in mice led to high death rates in the experimental animals, suggested by researchers to be the result of "oversaturation" of the dsRNA pathway. These considerations are under active investigation to mitigate their impact on the potential therapeutic applications of RNAi. One approach is to avoid oversaturation by using lower amounts of siRNa in combination with a drug-like, small organic molecule that affects the same pathway as the siRNA. To discover such drugs, the siRNA under investigation could be added to an OPS library under the uHTSS conditional paradigm described above, which will detect compounds that act in combination or synergistically with the siRNA under study.

In a particular embodiment of the instant invention, orthogonal pooled chemogenomic screening (OPCS) is used to profile drug candidates. At a time when pharmaceutical companies have limited resources to develop new and better drugs, they must continually evaluate the effectiveness and efficiency of their preclinical and clinical candidates. The nomination of a lead molecule to a viable drug candidate is a key step in the drug discovery/development continuum. Transition through this critical milestone requires the knowledge of the pharmacological action of the candidate, not only on the 'specific' target of its therapeutic actions, but also the specificity of the candidate on other targets. In fact, untoward, off-target affects that lead to safety concerns is perhaps the greatest problem in the entire pharmaceutical R&D continuum. A recent example is the withdrawal of Vioxx® due to safety concerns, which have not been resolved to any mechanism of action. There are estimated to be 3,000-10,000 drug-gable targets in the human genome, yet all drugs to date are believed to work through around 500 biological targets. Therefore, cross-activity testing lead candidates on every target is presently impossible.

Figure 6:
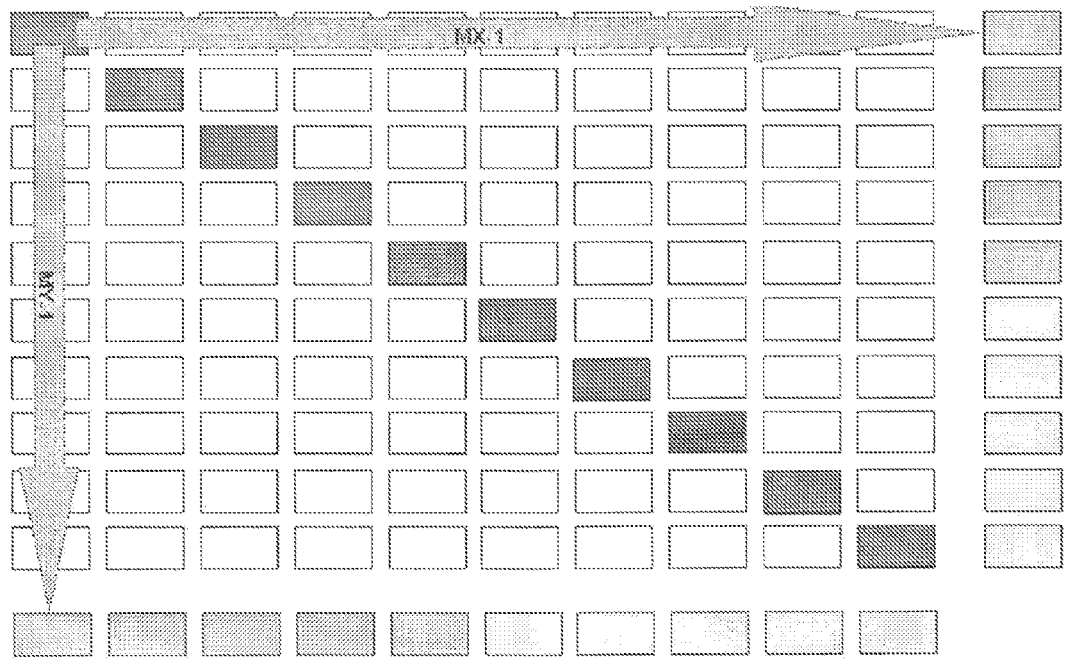
FIG. 6 depicts a method of 'mass-inclusion' of congeneric (structurally or pharmacologically similar) or pharmacologically active agents into orthogonal pools so that only one active or analogous agent appears in every well.

The instant invention of uHTSS accommodates the profiling of drug candidates using OPCS, which is a variation on conditioned uHTSS. The candidate under investigation is added to every well of a diversity-focused library (i.e., one containing reference agents and scaffolds with known activity on the major signal transduction pathways) and appropriate screens are run. For example, Vioxx® along with a small panel of prototypic non-steroidal anti-inflammatory drugs (NSAIDs), e.g. Celebrex® and Advil®, are each added (separately) as a conditioning agent to OPS libraries as depicted in FIG. 6, followed by evaluating their effects in cardiac ion channel assays ("Emerging Technologies for Ion Channels" (2005) Gen. Eng. Biotech. News 25:19). The objective is to record a differential activity profile between that of the library without added Vioxx® (i.e., uHTSS) and the activity pattern obtained when Vioxx® is included in OPS pools (the uHTSS variation of OPCS), thereby forming its specific OPCS signature which may be distinct from that of the other NSAIDs so tested. The profiling may be accomplished thus:

1. Run a conditioned screen with a drug candidate or an approved drug in a library-focused chemical collection of any number of compounds using the uHTSS paradigm. For this example, the activity profile of Vioxx® and up to four other NSAIDs, including Celebrex®, may be collected. Running five conditioned screens in the OPS format is the same effort as a single screen in the traditional n=1 HTS format, hence enabling 'ultra' (5× more efficient) HTS.

2. Determine which pools yield an active response in an appropriate assay, for example a cardiac ion channel HTS assay or other assay deemed relevant to illuminate how Vioxx® differs from other NSAIDs.

3. Perform the data analysis with the appropriate activity cutoffs as described for general OPS.

4. Determine differential orthogonal-correlated single compounds between the conditioning NSAIDs and the drug in question (e.g., Vioxx®).

5. Determine differential Orphan pools between the conditioning NSAIDs and the drug in question (e.g. Vioxx®).

Active pools discovered in Step #5 indicate a compound interacts with the NSAID in that Orphan pool. It is not obligatory to isolate synergistically active compounds from the discovered pools. The objective of OPCS is to use the random chemo-diversity in uHTSS to interrogate the combinatorial biology of cellular signaling pathways in appropriate cell assays to detect patterns of activity that distinguish drugs in the same pharmacological class that would otherwise be difficult to discriminate. It is possible to systematically resolve which of the compounds in the pool interact with the specific NSAID for all such pools observed in each of the panel of the five assays, but it would be difficult to do so manually by the methods described hereto. Once OPS data is in hand for the orthogonal-Actives and Orphan-pool actives, computational methods can help identify structural themes of compounds that interact with one another synergistically via the uHTSS approaches described above.

The 'chemical intelligence' of the OPS software that performs the triage analysis (as depicted in FIG. 3) may be complemented by considered application of decision tree analysis by recursive partitioning with an application such as Random Forest™ (Salford Systems Inc, San Diego, Calif.). This technology is a useful classification tool for predicting activities or activity classes in structure-activity relationship (SAR) analysis (16). At each decision point, molecules are split into two groups by a selection parameter in a recursive manner, until a threshold criterion is achieved. The speed and the 2-D nature of the approach are especially good for interrogating large commercial databases. U.S. Pat. No. 6,434,542 provides an example of how to implement the computational approach for simple 10-pools; however, it is impossible to separate single Actives from synergistic pairs. This is accomplished only after OPS is run and the orthogonally-correlated data for the compounds as taught by the instant invention is in hand, or classic n=1 HTS is run together with pooled HTS (i.e.; 'stacked screening), because it is critically important to extract all actives. The uHTSS method allows isolating orphan pools whose activity cannot be accounted for by singly-active compounds additively, so that probable synergistic pairs or higher order combinations can be isolated to the Orphan pools.

The next step is to resolve what target pathways are affected by the active pairs, for which classic structure-activity relationship (SAR) extraction and categorization principles are ideal. Structural similarity clustering of compounds from active pairs helps determine those features to be used as the basis for similarity searching of available databases for prototypic chemical agents with defined mechanisms, including DrugBank™, Wombat, KEGG, Pubchem and others (Marechal, E. (2008) Comb. Chem. High Throughput Screen 11:583-6) in order to develop a model consistent with SAR that defines the biological activity of active pairs. The goal here is to match the chemotype of the entities comprising active-pairs with a specific chemotype for known drugs (or reference agents known to modulate specific pathways) to develop a mechanism model for activity of the pairs. Qualifying reference drugs would be acquired and tested as combination pairs. If the SAR based mechanism model is correct, then the effect observed with paired screening hits should be recapitulated by replacing either or both paired members with the known agents as surrogates. If selective antagonists are available, and they abrogate activity, then the biological mechanism of the response comes into focus. The last step of the protocol is to characterize pharmacological mechanisms for additivity, synergism or potentiation. This requires cross-dilution-mixing matrices and is described elsewhere (Chou, T. C. (2006) Pharmacol. Rev. 58(3):621-81; Borisy et al. (2003) Proc. Natl. Acad. Sci., 100:7977-82).

DEFINITIONS

The following definitions are provided to facilitate an understanding of the present invention:

As used herein, the term "small molecule" refers to a substance or compound that has a relatively low molecular weight (e.g., less than 4,000 atomic mass units (a.m.u.), particularly less than 2,000 a.m.u.). Typically, small molecules are organic, but are not proteins, polypeptides, or nucleic acids, though they may be amino acids or dipeptides.

The term "isolated" may refer to a compound or complex that has been sufficiently separated from other compounds with which it would naturally be associated. "Isolated" is not meant to exclude artificial or synthetic mixtures from other compounds or materials, or the presence of impurities that do not interfere with fundamental activity or ensuing assays, and that may be present, for example, due to incomplete purification, or the addition of stabilizers.

"Nucleic acid" or a "nucleic acid molecule" as used herein refers to any DNA or RNA molecule, either single or double stranded and, if single stranded, the molecule of its complementary sequence in either linear or circular form.

"Antisense molecule" refers to a nucleic acid molecule that hybridizes to all or a portion of a target gene or all or a portion of an mRNA encoded by a target gene. Such antisense molecules are typically between 15 and 30 nucleotides in length and often span the translational start site of mRNA molecules.

"Small interfering RNA" (siRNA) refers to an RNA comprising between about 10-50 nucleotides which is capable of directing or mediating RNA interference. Typically, siRNA molecules are double stranded RNA molecules between about 15 and 30 nucleotides in length, particularly 18-25 nucleotides in length, particularly about 21 nucleotides in length. The nucleotide sequence of the siRNA molecules commonly begin from an AA dinucleotide sequence.

While certain of the preferred embodiments of the present invention have been described and specifically exemplified above, it is not intended that the invention be limited to such embodiments. Various modifications may be made thereto without departing from the scope and spirit of the present invention, as set forth in the following claims.

What is claimed is:

1. A method of identifying agents that exhibit synergy in an assay, said method comprising
   a) performing an orthogonally pooled screening assay on separate pooled mixtures of agents using said screening assay to measure the activity of the pooled mixtures, wherein every agent is present in at least two separate pooled mixtures in said orthogonal pooled screening assay;
   b) isolating an orphan active pooled mixture detected in step a), wherein said orphan active pooled mixture exhibits a threshold activity, and wherein all other pooled mixtures containing an agent from said orphan active pooled mixture do not exhibit said threshold activity;
   c) verifying said threshold activity of the orphan active pooled mixture of step b) by determining that the orphan active pooled mixture comprises agents for which the summation of the activities of the other pooled mixtures containing the individual agents not exhibiting said threshold activity of said orphan active pooled mixture is less than the level of said threshold activity of said orphan active pooled mixture isolated in step b) which exhibits said threshold activity, thereby identifying a verified orphan active pooled mixture; and
   d) testing individual agents and binary mixtures from the separated mixtures of agents comprising every possible pair of agents from all agents within the verified isolated orphan active pooled mixture having a threshold activity identified in step c);
   wherein the agents of step d) of a binary mixture exhibit synergy when the binary mixture exhibits greater activity in step d) than the sum of the individual activities of the agents in the orphan active pool not exhibiting said threshold activity in step c), wherein the activity of said orphan active pool is not accounted for by the additive activities of singly-active compounds.

2. The method of claim 1, further comprising individually testing each agent pooled in step a) for accomplishing step c) by cross-correlating the activities or lack thereof in the single-data with the activities observed in the pooled-data.

3. The method of claim 1, wherein the pooled mixtures of agents are pooled ten compounds per mixture.

4. The method of claim 1, wherein the screening is performed at multiple concentrations.

5. The method of claim 1, wherein every pooled mixture comprises an additional agent, wherein said additional agent is inactive.

6. The method of claim 5, wherein the additional agent is a nucleic acid molecule.

7. The method of claim 6, wherein said nucleic acid molecule is a small interfering ribonucleic acid (RNA).

8. The method of claim 5, wherein the additional agent is a small molecule.

9. The method of claim 5, wherein the additional agent is a Food and Drug Administration approved drug or a drug candidate in clinical trials.

10. The method of claim 1, wherein each pooled mixture contains three or more agents.

11. The method of claim 1, wherein the assay comprises detecting binding of one or more agents in the pools to a molecule.

12. The method of claim 11, wherein the molecule is a polypeptide or protein.

13. The method of claim 11, wherein the molecule is a nucleic acid molecule.

* * * * *